United States Patent
Najafi et al.

(10) Patent No.: US 10,383,575 B2
(45) Date of Patent: Aug. 20, 2019

(54) MINIMALLY-INVASIVE PROCEDURES FOR MONITORING PHYSIOLOGICAL PARAMETERS WITHIN INTERNAL ORGANS AND ANCHORS THEREFOR

(71) Applicant: Integrated Sensing Systems Inc., Ypsilanti, MI (US)

(72) Inventors: Nader Najafi, Ann Arbor, MI (US); Catherine Hook Morgan-Leonard, Tecumseh, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 427 days.

(21) Appl. No.: 15/186,930

(22) Filed: Jun. 20, 2016

(65) Prior Publication Data
US 2017/0095210 A1   Apr. 6, 2017

Related U.S. Application Data

(63) Continuation-in-part of application No. 14/873,288, filed on Oct. 2, 2015, now abandoned.

(51) Int. Cl.
| | |
|---|---|
| A61B 5/00 | (2006.01) |
| A61B 5/07 | (2006.01) |
| A61B 17/34 | (2006.01) |
| A61B 5/03 | (2006.01) |
| A61B 5/0215 | (2006.01) |
| G06F 19/00 | (2018.01) |
| A61M 5/172 | (2006.01) |
| G16H 40/67 | (2018.01) |

(52) U.S. Cl.
CPC .......... *A61B 5/6882* (2013.01); *A61B 5/0215* (2013.01); *A61B 5/036* (2013.01); *A61B 5/076* (2013.01); *A61B 5/6869* (2013.01); *A61B 17/3468* (2013.01); *G06F 19/00* (2013.01); *A61B 5/0022* (2013.01); *A61B 5/0031* (2013.01); *A61B 5/031* (2013.01); *A61B 5/4839* (2013.01); *A61B 5/6868* (2013.01); *A61B 5/746* (2013.01); *A61B 2560/0214* (2013.01); *A61B 2560/0219* (2013.01); *A61B 2562/028* (2013.01); *A61B 2562/0247* (2013.01); *A61B 2562/085* (2013.01); *A61B 2562/162* (2013.01); *A61M 5/1723* (2013.01); *G16H 40/67* (2018.01)

(58) Field of Classification Search
CPC ..... A61B 5/6882; A61B 5/0215; A61B 5/076; A61B 5/6869; A61B 17/3468
See application file for complete search history.

(56) References Cited

U.S. PATENT DOCUMENTS

| | | | |
|---|---|---|---|
| 7,860,579 B2 | 12/2010 | Goetzinger et al. | |
| 2013/0144379 A1* | 6/2013 | Najafi | A61B 5/0024 623/2.11 |

* cited by examiner

*Primary Examiner* — William H Matthews
(74) *Attorney, Agent, or Firm* — Hartman Global IP Law; Gary M. Hartman; Domenica N. S. Hartman (57) ABSTRACT

Minimally-invasive surgical procedures for monitoring physiological parameters within internal organs of living bodies, and anchors therefor. Such an anchor may have a tubular portion defining a distal end of the anchor, a disk-shaped portion having a proximal surface at a proximal end of the anchor, and an internal passage within the tubular and disk-shaped portions for receiving a sensing device. The internal passage has a proximal portion and an oppositely-disposed distal portion that defines a distal opening in the tubular portion that is configured to retain the sensing device within the internal passage, in combination with one or more features at the proximal end of the anchor. One or more features are defined on the disk-shaped portion for securing the anchor to the wall of the internal organ.

25 Claims, 7 Drawing Sheets

MINIMALLY-INVASIVE PROCEDURES FOR MONITORING PHYSIOLOGICAL PARAMETERS WITHIN INTERNAL ORGANS AND ANCHORS THEREFOR

CROSS REFERENCE TO RELATED APPLICATIONS

This is a continuation-in-part patent application of co-pending U.S. patent application Ser. No. 14/873,288, filed Oct. 2, 2015, whose contents are incorporated herein by reference.

BACKGROUND OF THE INVENTION

The present invention generally relates to implantable medical devices, monitoring systems and implantation procedures. More particularly, this invention relates to a minimally-invasive surgical procedure for implanting a sensing device adapted to monitor one or more physiological properties of a living body, such as pressure, temperature, flow, acceleration, vibration, composition, and other properties of biological fluids within an internal organ.

Various implantable devices have been developed to monitor and wirelessly communicate physiological parameters of the heart, as well as physiological parameters of other internal organs, including the brain, bladder and eyes. Such predicate wireless devices can generally be divided into two functional categories: large-sized (pacemaker-type) and smaller-sized telemetric devices. An example of a pacemaker-type wireless pressure sensor is the LVP-1000 Left Ventricular Pressure Monitoring System under development by Transoma Medical, Inc. The LVP-1000 comprises a sensor adapted to be implanted into an external wall of the heart, a wireless transmitting unit adapted to be located elsewhere within the patient, and wiring that physically and electrically connects the sensor and transmitting unit. The sensor of the LVP-1000 is adapted to be secured with sutures to the left side of the heart during an open-chest surgical procedure.

Smaller telemetric sensors include batteryless pressure sensors developed by CardioMEMS, Inc., Remon Medical, and the assignee of the present invention, Integrated Sensing Systems, Inc. (ISSYS). For example, see commonly-assigned U.S. Pat. Nos. 6,926,670 and 6,968,734 to Rich et al., and N. Najafi and A. Ludomirsky, "Initial Animal Studies of a Wireless, Batteryless, MEMS Implant for Cardiovascular Applications," Biomedical Microdevices, 6:1, p. 61-65 (2004). With such technologies, pressure changes are can be sensed with an implant equipped with a mechanical capacitor (tuning capacitor) having a fixed electrode and a moving electrode, for example, on a diaphragm that deflects in response to pressure changes. The implant is further equipped with an inductor in the form of a fixed coil that serves as an antenna for the implant, such that the implant is able to receive radio frequency (RF) signals from outside the patient and transmit the frequency output of the circuit. The implant can be placed directly within the heart chamber whose pressure is to be monitored, or in an intermediary structure such as the atrial or ventricular septum. Implantation involves a translumenal implantation technique using a placement catheter to deliver the implant to a chamber of the heart or another cardiovascular chamber, after which the implant is secured to an interior wall surface of the chamber.

Figure 1A:
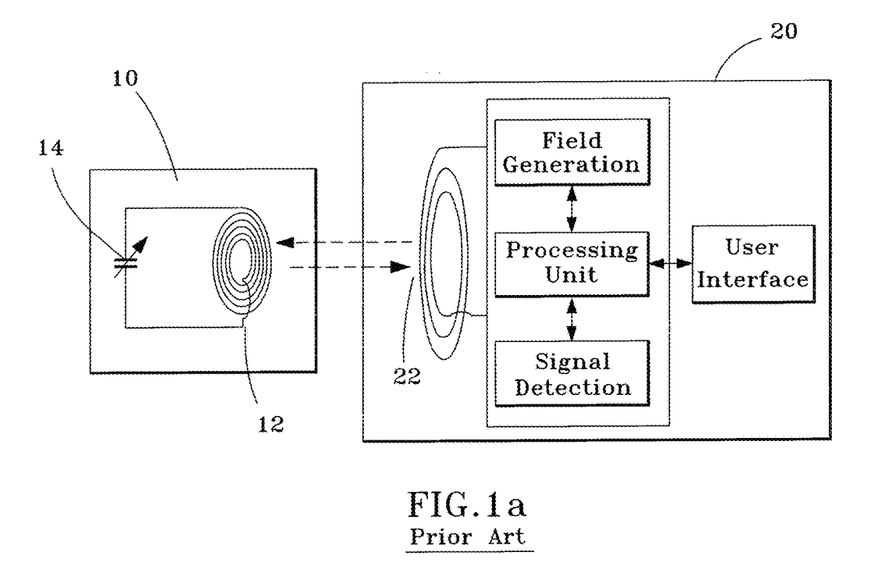
FIGS. 1a and 1b are block diagrams of wireless pressure monitoring systems that utilize resonant and passive sensing schemes, respectively, which can be utilized by monitoring systems of this invention.
Figure 1B:
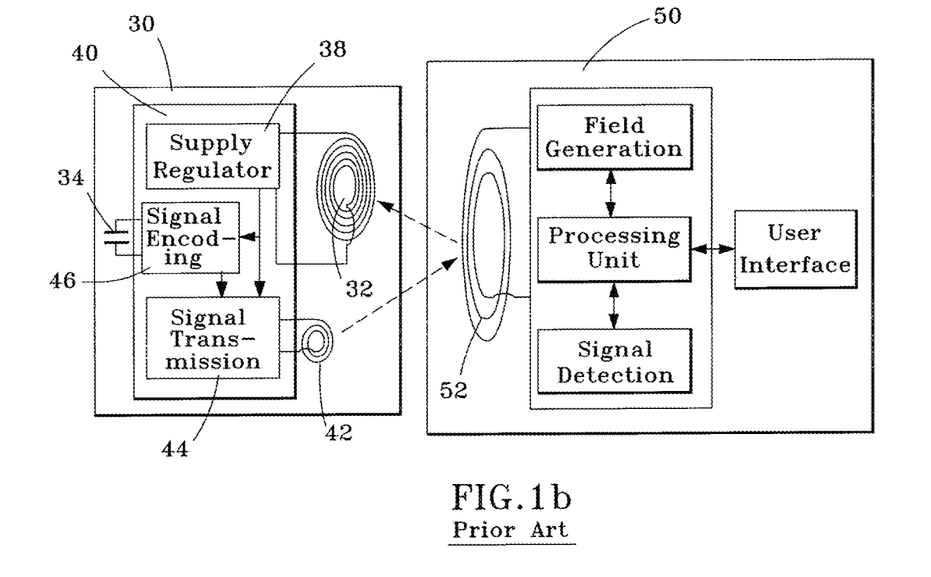

FIGS. 1a and 1b represent two types of wireless pressure sensing schemes disclosed in the Rich et al. patents. In FIG. 1a, an implant 10 is shown as operating in combination with a non-implanted external reader unit 20, between which a wireless telemetry link is established using a resonant scheme. The implant 10 contains a packaged inductor coil 12 and a pressure sensor in the form of a mechanical capacitor 14. Together, the inductor coil 12 and capacitor 14 form an LC (inductor-capacitor) tank resonator circuit that has a specific resonant frequency, expressed as $1/(LC)^{1/2}$, which can be detected from the impedance of the circuit. At the resonant frequency, the circuit presents a measurable change in magnetically-coupled impedance load to an external coil 22 associated with the reader unit 20. Because the resonant frequency is a function of the capacitance of the capacitor 14, the resonant frequency of the LC circuit changes in response to pressure changes that alter the capacitance of the capacitor 14. Based on the coil 12 being fixed and therefore having a fixed inductance value, the reader unit 20 is able to determine the pressure sensed by the implant 10 by monitoring the resonant frequency of the circuit.

FIG. 1b shows another wireless pressure sensor implant 30 operating in combination with a non-implanted external reader unit 50. A wireless telemetry link is established between the implant 30 and reader unit 50 using a passive, magnetically-coupled scheme, in which on-board circuitry of the implant 30 receives power from the reader unit 50. In the absence of the reader unit 50, the implant 30 lays passive and without any internal means to power itself. When a pressure reading is desired, the reader unit 50 must be brought within range of the implant 30.

In FIG. 1b, the implant 30 contains a packaged inductor coil 32 and a pressure sensor in the form of a mechanical capacitor 34. The reader unit 50 has a coil 52 by which an alternating electromagnetic field is transmitted to the coil 32 of the implant 30 to induce a voltage in the implant 30. When sufficient voltage has been induced in the implant 30, a rectification circuit 38 converts the alternating voltage on the coil 32 into a direct voltage that can be used by electronics 40 as a power supply for signal conversion and communication. At this point the implant 30 can be considered alert and ready for commands from the reader unit 50. The implant 30 may employ the coil 32 as an antenna for both reception and transmission, or it may utilize the coil 32 solely for receiving power from the reader unit 50 and employ a second coil 42 for transmitting signals to the reader unit 50. Signal transmission circuitry 44 receives an encoded signal generated by signal conditioning circuitry 46 based on the output of the capacitor 34, and then generates an alternating electromagnetic field that is propagated to the reader unit 50 with the coil 42.

The implant 30 is shown in FIG. 1b without a battery, and therefore its operation does not require occasional replacement or charging of a battery. Instead, the energy required to perform the sensing operation is entirely derived from the reader unit 50. However, the implant 30 of FIG. 1b could be modified to use a battery or other power storage device to power the implant 30 when the reader unit 50 is not sufficiently close to induce a voltage in the implant 30, in which case the wireless telemetry link between the implant 30 and reader unit 50 uses an active magnetically-coupled scheme.

BRIEF SUMMARY OF THE INVENTION

The present invention provides anchors capable of use in a minimally-invasive surgical procedure in which a miniature implantable sensing device is implanted to monitor one or more physiological parameters within an internal organ of a living body, such as the human heart, brain, kidneys, lungs, bladder, etc. Such a procedure entails placing the sensing device through an external wall of the organ, such as a wall of the heart, blood vessel, kidneys, lungs, bladder, etc., or a wall surrounding the organ, such as the abdominal wall or the meninges surrounding the brain.

According to one aspect, the anchor has a tubular portion defining a distal end of the anchor, a disk-shaped portion having a proximal surface at a proximal end of the anchor, and an internal passage within the tubular and disk-shaped portions for receiving a sensing device. The internal passage has a distal portion that defines a distal opening in the tubular portion at the distal end of the anchor, and has a proximal portion at the proximal end of the anchor. The distal opening is configured to retain the sensing device within the internal passage. The anchor further includes means at the proximal end of the anchor for retaining the sensing device within the internal passage, and means on the disk-shaped portion for securing the anchor to the wall of the internal organ.

Other aspects of the invention include minimally-invasive surgical procedures that use an anchor comprising the elements described above to place a miniature implantable sensing device through an external wall of an organ to enable the sensing device to monitor one or more physiological parameters within the organ.

Minimally-invasive surgical procedures and sensing devices that utilize the anchor are preferably intended to be particularly well-suited for providing safe, fast, detailed, real-time, and continuous measurements for both short-term and long-term applications, such as over a period of hours, days, weeks or longer in an emergency room or hospital. In cases where the patient is moved to a rehabilitation facility, the sensing device can be utilized for much longer periods and data relating to the physiological parameter(s) being monitored can be wirelessly sent to a physician or nurse in order to provide diagnostic tailored treatment of the patient. For patients that need even longer term monitoring, at-home monitoring can be easily accomplished by tying a readout device to the Internet, telephone, or other long-distance communication system. The sensing device can be configured for batteryless operation, allowing the device to potentially function for a patient's lifetime with no maintenance or need for replacement after initial implantation.

Miniaturization of the sensing device can be effectively achieved by fabricating the sensing device to have a miniature MEMS (micro-electromechanical system) sensing element, combined with custom electronics and a telemetry antenna. Preferred aspects of the invention include limiting the volume protrusion of the anchor and sensing device into the cavity being monitored. In the case of the heart, the risk of thrombogenesis can be significantly reduced by limiting protrusion of the anchor and sensing device into the blood stream within a heart chamber, in terms of distance into the cavity as well as shape and size of the protruding portion of the anchor and/or sensing device. For this purpose, the sensing device is preferably configured so that the sensing element is located on a distal surface (relative to insertion direction) of the device, such that only the distal surface of the sensing device need contact the biological fluid being monitored.

Implantation procedures and sensing systems of this invention can be used to measure a variety of physiological parameters, a particularly notable example of which is physiological pressures such as cardiovascular pressures, intracranial pressures, intra-sac pressures, radial artery pressure, pulmonary artery pressure, etc. A preferred aspect of the invention is that only a small portion of the sensing system—namely, the sensing device and its anchor—need be implanted inside the body, with only a portion thereof actually being within the organ, while the remaining members of the system, such as a readout unit, are located outside the organ and, in the case of a readout unit, outside the body. As a result, the procedure for implanting the sensing device as well as the device itself and its anchor are minimally invasive, which allows greater flexibility in the implant location and allows the sensing device to be used in many areas and organs of the body, including the heart. When used in the heart, the sensing device and anchor greatly reduce the risk of complications, in particular thrombosis and thrombogenicity.

Other aspects and advantages of this invention will be better appreciated from the following detailed description.

BRIEF DESCRIPTION OF THE DRAWINGS

FIG. 12 is a cross-sectional view taken along line 12-12 in FIG. 11, FIG. 13 schematically represents a manner in which the bolt-type anchor of FIGS. 10 through 12 can be assembled with the sensing device of FIG. 4 to form a sensing unit, and FIG. 14 schematically represents the resulting sensing unit.

DETAILED DESCRIPTION OF THE INVENTION

Illustrated in FIGS. 2a through 14 are monitoring systems and components thereof that implement one or more implantable sensors configured to be placed through an external wall of an internal organ for monitoring one or more physiological parameters within an internal cavity of the organ. Organs of particular interest include but are not limited to the heart, brain, kidneys, lungs, and bladder. The physical footprint of the implanted portion of each monitoring system is limited to the sensing device, its anchor and optionally a separate antenna, such that the sensing unit can be far smaller than, for example, the Transoma Medical, Inc., LVP-1000 Left Ventricle Pressure Monitoring System, which must be physically connected to a relatively large remote transmitting device.

Figure 2A:
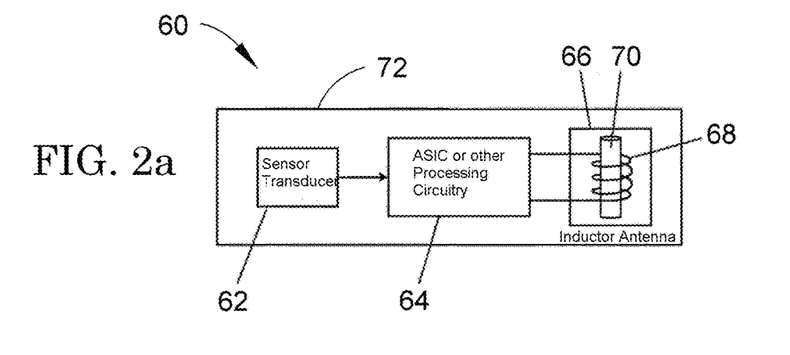
FIGS. 2a and 2b are schematic representations of wireless sensing devices suitable for use in wireless monitoring systems of this invention.

While the resonant, passive and active schemes described in reference to FIGS. 1a and 1b are also within the scope of the invention, sensing devices of this invention are preferably passive and preferably translate a physiologic parameter into a frequency tone and modulate the impedance of an antenna with the frequency tone to communicate the physiologic parameter to an external readout unit. FIG. 2a represents a wireless implantable sensing device 60 as comprising a transducer 62, electronic circuitry 64 (e.g., an application specific integrated circuit, or ASIC), and an antenna 66. These and any additional or optional components (e.g., additional transducers) of the sensing device 60 are preferably contained in a single sealed housing 72. The antenna 66 is shown as comprising a coil 68 (e.g., copper windings) wrapped around a core 70 (e.g., ferrite), though other antenna configurations and materials are foreseeable. The transducer 62 is preferably a MEMS device, more particularly a micromachine fabricated by additive and subtractive processes performed on a substrate. The substrate can be rigid, flexible, or a combination of rigid and flexible materials. Notable examples of rigid substrate materials include glass, semiconductors, silicon, ceramics, carbides, metals, hard polymers, and TEFLON. Notable flexible substrate materials include various polymers such as parylene and silicone, or other biocompatible flexible materials. A particular but nonlimiting example of the transducer 62 is a MEMS capacitive pressure sensor for sensing pressure, such as various blood pressures within the heart, intracranial pressure, intraocular pressure, etc., though other materials and any variety of sensing elements, e.g., capacitive, inductive, resistive, piezoelectric, etc., could be used. For example, the transducer 62 could be configured to sense temperature, flow, acceleration, vibration, pH, conductivity, dielectric constant, and chemical composition, including the composition and/or contents of a biological fluid, for example, oxygen, carbon dioxide, glucose, gene, hormone, or gas content of the fluid. The sensing device 60 may be powered with a battery or other power storage device, but in preferred embodiments is powered entirely by a remote device that is not configured for implantation, such as a readout unit 80 represented in FIG. 2c.

Figure 2B:
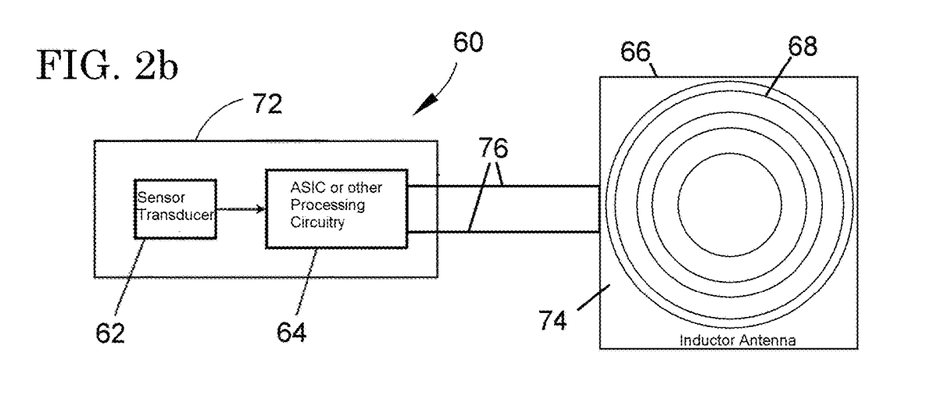
Figure 2C:
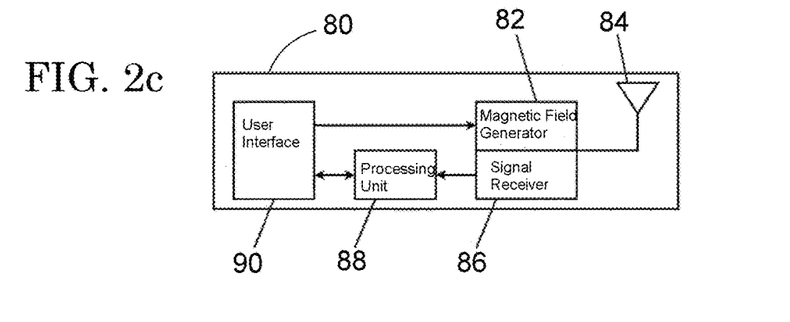
FIG. 2c is a schematic representation of a readout device suitable for use in wireless monitoring systems of this invention.

Because the sensing device 60 is equipped with a built-in antenna 66, the device 60 requires only an anchor for implantation, and does not require a wire, cable, tether, or other physical component that conducts the output of the sensing device 60 to a separate location where another component utilizes the output of the sensing device and/or transmits the output of the sensing device to a location outside the body of the patient. In FIG. 2b, consistent reference numbers are used to identify functionally equivalent structures of a second wireless implantable sensing device 60 that differs from the device 60 of FIG. 2a by the placement of the antenna 66 outside the housing 72. The antenna 66 is shown as comprising a conductive coil 68 patterned on a substrate 74, and connected to the device 60 with wires 76. The substrate 74 can be rigid, flexible, or a combination of rigid and flexible materials such as those described above in reference to the transducer 62, and may carry additional electronics. The antenna 66 can be placed remotely from the sensing device 60, such as immediately under the skin, to provide better wireless transmission between the device 60 and the readout device 80 of FIG. 2c. A remotely-placed antenna for use with the invention can also be configured in accordance with the antenna 66 as shown in FIG. 2a, with a coil 68 wrapped around a core 70 and connected to the device 60 with wires 76.

In addition to powering the sensing device 60, the readout unit 80 is represented as being configured to receive an output signal from the sensing device 60, process the signal, and relay the processed signal as data in a useful form to a user. The readout unit 80 is shown equipped with circuitry 82 that generates a high-frequency (e.g., 13.56 MHZ), high-power signal for an antenna 84 to create the magnetic field needed in communicate with the sensing device 60. The readout unit 80 contains additional circuitry 86 to receive and demodulate a backscattered signal from the sensing device 60, which is demodulated and then processed with a processing unit 88 using calibration coefficients to quantify the physiological parameter of interest. The readout unit 80 is further shown as being equipped with a user interface 90, by which the operation of the readout unit 80 can be controlled to allow data logging or other user control and data examination.

Figure 3:
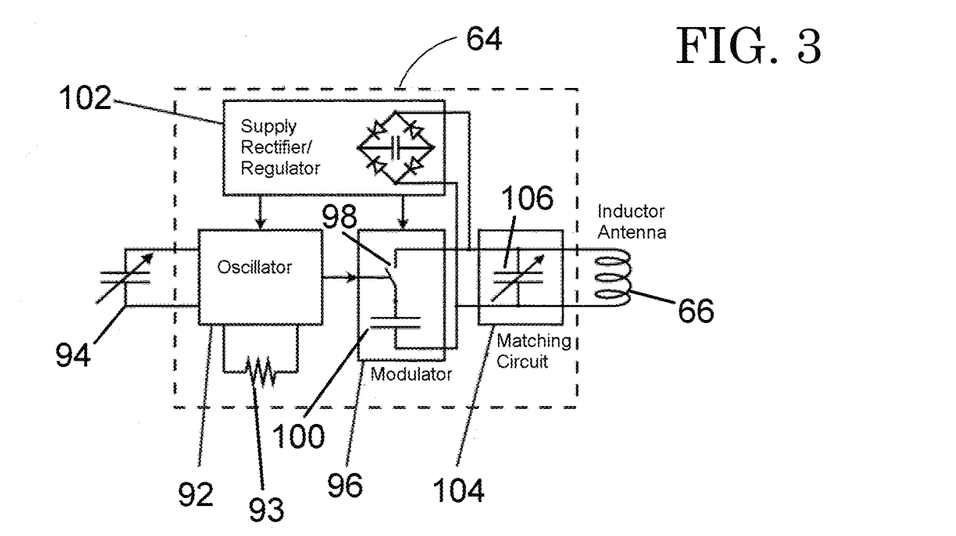
FIG. 3 schematically represents internal components of processing circuitry suitable for use in the sensing devices of FIGS. 2a and 2b.

FIG. 3 represents a block diagram showing particularly suitable components for the electronic circuitry 64 of FIGS. 2a and 2b. The circuitry 64 includes an oscillator 92, for example a relaxation oscillator, connected to a resistor 93 and a MEMS mechanical capacitor 94. A preferred MEMS capacitor 94 comprises a fixed electrode and a moving electrode on a diaphragm that deflects relative to the fixed electrode in response to pressure, such that the capacitor 94 is able to serve as a pressure sensing element for the transducer 62. A nonlimiting example of a preferred MEMS capacitor 94 has a pressure range of about −100 to about +300 mmHg, with an accuracy of about 1 mmHg. Alternatively, a variable resistor transducer could be used with a fixed capacitance, or an inductor could be substituted for the transducer or fixed circuit element. Based on the RC or other time constant ($1/(LC)^{1/2}$), the oscillator 92 produces a frequency tone that directly relates to the capacitive value of the capacitor 94 and, therefore, the physiologic parameter of interest.

The circuitry 64 is further shown as including a modulator 96, with which the frequency tone of the oscillator 92 is encoded on a carrier frequency, placed on the antenna 66, and then transmitted to the readout unit 80. This is accomplished simply by opening and closing a switch 98 and adding a capacitance 100 to the antenna matching circuit, resulting in an AM (amplitude modulation) LSK (load shift keying) type modulation. This transmission approach is similar to that used in RFID (radio frequency identification) communications, except RFID does not typically encode analog information but instead encodes a few digital bits either on an AM LSK or FSK (frequency shift keying) modulation.

Because the preferred embodiment of the sensing device 60 does not utilize wires to transmit data or power to the readout unit 80, nor contains an internal power source, the circuitry 64 further includes a regulator/rectifier 102 to extract its operating power from an electromagnetic (EM) waves generated by the readout unit 80 or another EM power source. The regulator/rectifier 102 rectifies incoming power from the inductive antenna 66 and conditions it for the other circuit components within the circuitry 64. Finally, a matching circuit 104 is shown as comprising a trimmable capacitor bank 106 to resonate the inductor antenna 66, which is energized by the magnetic field and backscatters data as previously described.

As an alternative to the embodiment of FIG. 3, the modulator 96 could use a 13.56 MHZ (or other frequency) magnetic field as a clock reference to create a second carrier frequency, such as one that is one-quarter or another sub-multiple or multiple of the original frequency. The second carrier frequency can then be amplitude modulated (AM) using the oscillator frequency tone and transmitted to the readout unit 80 via the same antenna 66. In this embodiment, the readout unit 80 may or may not have a second antenna to receive the second carrier frequency-based AM signal.

The communication scheme described above differs from resonate tank communication systems that use capacitive pressure transducer elements in conjunction with an inductor/antenna. In particular, the circuitry 64 allows the use of any frequency for the high power readout unit 80, which in preferred embodiments utilizes an industrial, scientific, medical (ISM) band frequency. In contrast, the frequencies and potentially large bandwidths required of resonate tank communication systems are subject to FCC emission limitations, likely requiring the use of extra shielding or potentially other measures taken in the facilities where the sensing device 60 and readout unit 80 are to be used. Another feature of the circuitry 64 is the allowance of more combinations of oscillator elements to be used. Because resonator tank systems require an inductive element and a capacitive element in which at least one of the elements serves as a transducer, resonator tank systems do not lend themselves well to resistive-based or other based sensors. Finally, the circuitry 64 also allows for signal conditioning, such as transducer compensation, which allows for such items as removing temperature dependence or other non-idealities that may be inherent to the transducer 62. In the preferred embodiment, a negative temperature coefficient of the MEMS capacitor 94 can be compensated with simple circuitry relying on the positive temperature coefficient of resistor elements arranged in a trimmable bank of two resistor units with largely different temperature coefficients that can be selectively added in a trimming procedure in production to select the precise level to compensate the transducer variation.

In the past, the restrictive levels of energy available to small implantable medical sensing devices and the desire to maximize data rates to capture more detailed physiological parameter response have been met with a robust type of analog communication that places information on the frequency rather than amplitude of the carrier. In U.S. Pat. No. 6,929,970 to Rich et al., a secondary carrier frequency is used for communication with an interrogator unit, resulting in a technique that consumes substantially more power in the implant and requires a second external antenna to receive the signal. The greater power consumption of the implant necessitates a tradeoff between smaller size and longer communication range. In contrast, the communication scheme described above for this invention draws upon the RFID-type communications, such as those described in U.S. Pat. Nos. 7,015,826 and 6,622,567, whose contents are incorporated herein by reference. However instead of communicating digital data using a fixed rate clock, the present invention transmits analog information as the frequency of the clock to lower power consumption and enhance powering and communication range. In this way, much of the readout unit 80 can utilize hardware that is commercially available for RFID, except that a different demodulator is required. An early example of RFID can be found in U.S. Pat. No. 4,333,072.

Figure 4:
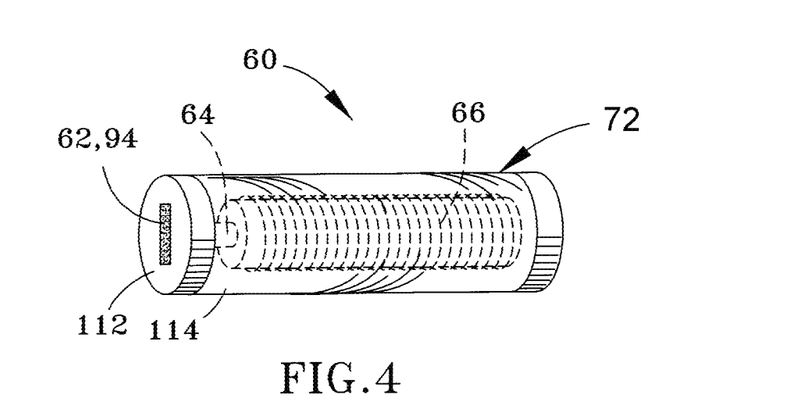
FIG. 4 represents a perspective view of a cylindrical self-contained sensing device of the type represented in FIGS. 2a and 2b.

FIG. 4 depicts a preferred example of the housing 72 as having a cylindrical shape with a flat distal face 112. (The terms "distal" and "proximal" are used herein in reference to orientation during the implantation procedure described below.) Other shapes are also possible, for example, a torpedo-shape in which the peripheral face 114 of the housing 72 immediately adjacent the distal face 112 is tapered or conical (not shown). The housing 72 can be formed of glass, for example, a borosilicate glass such as Pyrex Glass Brand No 7740 or another suitably biocompatible material. A biocompatible coating, such as a layer of a hydrogel, titanium, nitride, oxide, carbide, silicide, silicone, parylene and/or other polymers, can be deposited on the housing 72 to provide a non-thrombogenic exterior for the biologic environment in which the sensing device 60 will be placed. As can be seen in FIG. 4, the inductive antenna 66 (comprising the copper coil 68 surrounding the core 70 of FIG. 2a) occupies most of the internal volume of the housing 72. The size of the antenna 66 is governed by the need to couple to a magnetic field to enable telepowering with the readout unit 80 from outside the body, for example, a transmission distance of about 10 cm or more. The cylindrical shape of the housing 72 is convenient for the sensing device 60 to be endoscopically placed with anchors discussed in reference to FIGS. 5 through 14. The circuitry 64 is disposed between the antenna 66 and an end of the housing 72 that preferably carries the transducer 62. A nonlimiting example of an overall size for the housing 72 is about 3.7 mm in diameter and about 16.5 mm in length.

A preferred aspect of the invention is to locate the transducer 62 on a distal surface of the sensing device 60, for example, the flat distal face 112 of the cylindrical housing 72, or on the peripheral face 114 of the housing 72 immediately adjacent the distal face 112. In a preferred embodiment, the flat distal face 112 is defined by a biocompatible semiconductor material, such as a heavily boron-doped single-crystalline silicon, in whose outer surface the pressure-sensitive diaphragm (or other sensing element 94) is formed. In this manner, only the distal face 112 of the housing 72 need be in contact with a biological fluid whose physiological parameter is to be monitored. In the case of monitoring pressure within the heart, this aspect of the invention can be utilized to minimize protrusion of the sensing device 60 into the heart chamber, thereby reducing the risk of thrombogenesis.

FIGS. 5 through 14 represent embodiments for anchors with which the sensing device 60 of FIG. 4 can be anchored to a wall of an internal organ, for example, by making an incision in the wall from the exterior of the organ, inserting the sensing device 60 in the incision from the exterior side of the wall, and then securing the sensing device 60 to the wall. According to a preferred aspect of the invention, access to the organ and implantation of the sensing device 60 is achieved using an endoscope, for example, via laparoscopic surgery, thoracoscopic surgery, or another similar minimally-invasive procedure, as opposed to translumenal implantation techniques using a placement catheter that places a sensing device within an organ and then secures the device to an interior wall surface of the organ. As an endoscopic procedure, an endoscope or other suitable instrument comprising a rigid or flexible tube is utilized to enable the procedure to be visual observed, as well as the use of instruments for making the incision and securing the anchor as required by the invention. The procedure can be performed through small incisions (on the order of a few centimeters, for example, about three centimeters or less) as compared to much larger incisions needed in traditional surgical procedures. The procedure may entail insufflation of the body cavity surrounding the organ to create a working and viewing space for implantation and securement of the sensing device 60.

Together, the sensing device 60 and the anchors of FIGS. 5 through 14 form sensing units that have minimal protrusion into the organ when implanted through the organ wall from the exterior of the organ. Maximum protrusion of the sensing units is preferably not more than one centimeter, more preferably not more than eight millimeters, for example between about 0.5 to about 2 millimeters, with a preferred volumetric protrusion of not more than about 0.02 cm³. The distal end of the sensing units (for example, as defined by the distal face 112 of the housing 72 and/or the distal end of the anchor) may also be slightly recessed below the internal surface of the wall, for example, up to about two millimeters from the internal surface of the wall. Particularly suitable materials for the anchors include but are not limited to polymers including parylene, silicone, PEEK (polyether ether ketone), and polytetrafluoroethylene (PTFE), metals including NITINOL, glass, ceramics, and other biocompatible materials.

Figure 5:
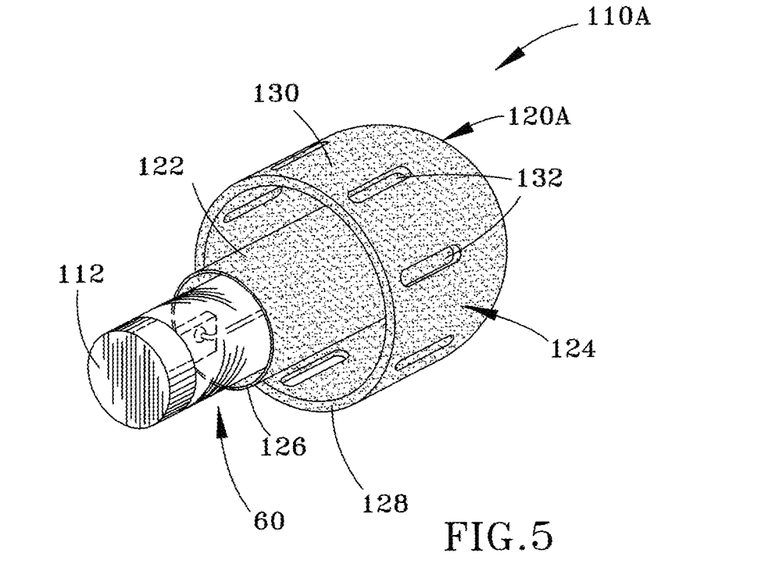
FIG. 5 schematically represents the sensing device of FIG. 4 assembled with a dome-type anchor to form a sensing unit ready for implantation in accordance with a first embodiment of the invention.
Figure 6:
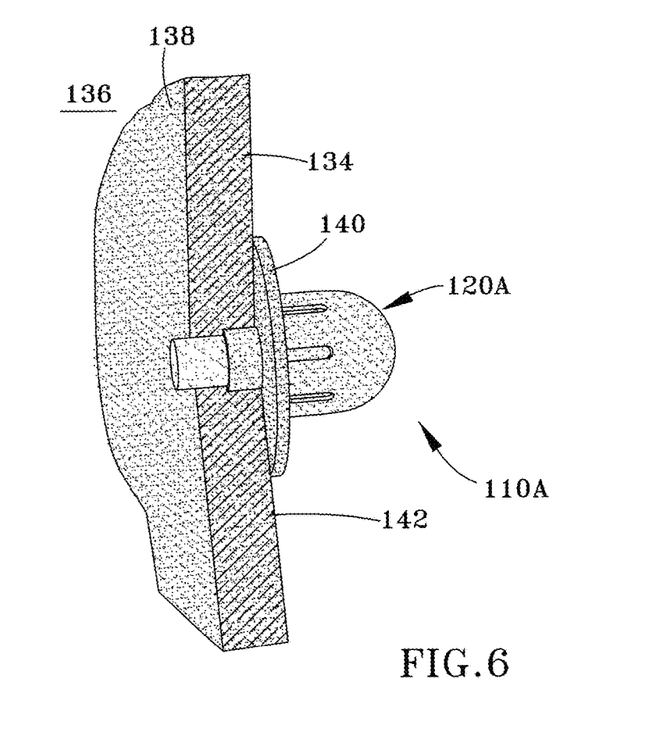
FIG. 6 schematically represents the sensing unit of FIG. 5 implanted in a wall of an internal organ in accordance with the first embodiment of the invention.

In FIGS. 5 and 6, an anchor 120A is shown configured to have a distal tubular portion 122 partially surrounded by a proximal dome-shaped portion 124. The anchor 120A is preferably in accordance with the teachings of commonly-assigned U.S. patent application Ser. No. 12/111,954 to Najafi et al., whose contents regarding anchor construction and use are incorporated herein by reference. The sensing device 60 is axially disposed within the tubular portion 122 to yield a sensing unit 110A in which the distal face 112 carrying the transducer 62 protrudes from the tubular portion 122. The sensing device 60 can be secured in the tubular portion 122 by any suitable means, such as an interference fit, a biocompatible epoxy, glue or cement, or any other type of attachment method or combinations of attachment methods known to those skilled in the art. The dome-shaped portion 124 generally joins the tubular portion 122 at an end 125 opposite the open end 126 of the tubular portion 122 through which the sensing device 60 is received. The dome-shaped portion 124 defines a substantially tubular section 130 that circumscribes the tubular portion 122 and terminates at an edge 128 short of the open end 126 of the tubular portion 122. Multiple oblong openings 132 are defined in the tubular section to enable the anchor 120A to be secured to a wall of an internal organ, such as with standard surgical sutures or another suitable attachment technique that can be performed during the endoscopic procedure, such as nails, screws, springs, and biocompatible adhesives such as cements, glues, epoxies, etc.

FIG. 6 depicts the sensing unit 110A of FIG. 5 implanted in an incision in a wall 134 of an internal organ for the purpose of sensing a physiological parameter of a biological fluid within an internal cavity 136 of the organ. The wall 134 may be an exterior wall of the heart, a blood vessel, kidneys, lungs, bladder, etc., or a wall surrounding an organ, such as the abdominal wall or the meninges surrounding the brain. As evident from FIG. 6, only the tubular portion 122 of the anchor 120A is inserted into the incision, and the dome-shaped portion 124 remains entirely outside the incision; as such, the tubular and dome-shaped portions 122 and 124 are not configured to clamp the wall 134 therebetween. Furthermore, the anchor 120A does not protrude through the wall 134, but instead is recessed in the wall 134, whereas the distal face 112 of the sensing device 60 protrudes into the internal cavity 136 of the organ. As noted above, the distance the distal face 112 protrudes from the internal surface 138 of the wall 134 (for example, the endocardium lining a chamber of the heart) is preferably not more than one centimeter, and more preferably not more than eight millimeters. As also noted above, the sensing device 60 and anchor 120A could be configured so that the anchor 120A, and not the sensing device 60, protrudes beyond the wall 134, in which case the distal face 112 of the sensing device 60 may be recessed up to about two millimeters from the internal surface 138 of the wall 134. Again, the anchor 120A preferably does not protrude more than one centimeter, and more preferably not more than eight millimeters, beyond the internal surface 138 of the wall 134. Finally, it is within the scope of the invention that both the anchor 120A and the sensing device 60 could protrude into the internal cavity 136, or that neither the anchor 120A nor the sensing device 60 protrudes into the internal cavity 136, but instead are recessed in the wall 134.

FIG. 6 further shows the inclusion of a felt pad 140 between the peripheral edge 128 of the anchor 120A and the external surface 142 of the wall 134. A suitable material for the felt pad 140 is standard surgical grade felt. The anchor 120A and the felt pad 140 can be simultaneously attached (e.g., sutured) to the wall 134. Depending on the material from which it is formed, the felt pad 140 may be used to promote cell (tissue) growth and encapsulation of the incision, leading to further stabilization of the sensing unit 110A.

Figure 7:
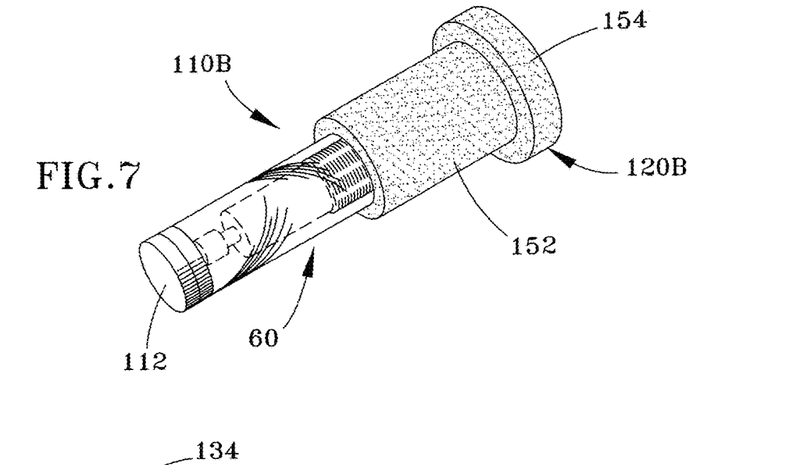
FIG. 7 schematically represents the sensing device of FIG. 4 assembled with a bolt-type anchor in accordance with a second embodiment of the invention.
Figures 8, 9:
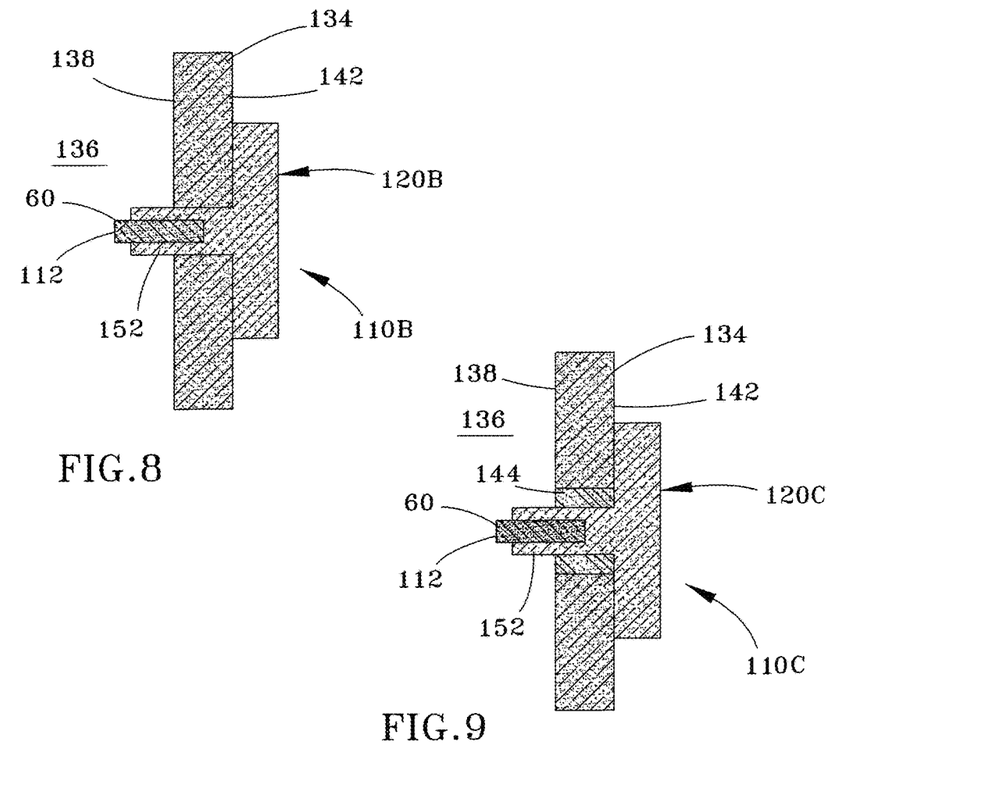
FIGS. 8 and 9 schematically represent sensing units equipped with bolt-type anchors implanted in a wall of an internal organ in accordance with the second embodiment of the invention.

FIGS. 7 and 8 show an anchor 120B that is again configured to have a distal tubular portion 152, but with a proximal disk-shaped portion 154, resulting in what will be referred to herein as a "bolt-type" anchor. Such an anchor is also disclosed in commonly-assigned U.S. patent application Ser. No. 12/111,954 to Najafi et al. As before, the sensing device 60 is shown axially disposed within the tubular portion 152, yielding a sensing unit 110B in which the distal face 112 of the device 60 carrying the transducer 62 protrudes from the tubular portion 152. Though not shown, the disk-shaped portion 154 may be formed to have multiple oblong openings to enable the anchor 120B to be secured to the wall 134 of an internal organ, such as with sutures or another suitable attachment technique that can be performed during the surgical procedure. In FIG. 9, a sensing unit 110C essentially identical to the unit 110B of FIGS. 7 and 8 is shown as further including a tubular insert 144 secured in the incision prior to placement of the remainder of the unit 110C. The insert 144 can be attached to the wall 134 with an interference fit, or with the use of a biocompatible cement, glue or epoxy, screws, springs, nails, etc. The tubular portion 152 of the bolt-type anchor 120C can then be secured within the bore of the insert 144. A preferred aspect of this embodiment is that the anchor 120C is not permanently joined to the insert 144 to permit the exchange of the sensing unit 110C and/or its sensing device 60, and/or the use of a different anchor with additional features.

As evident from FIGS. 8 and 9, both anchors 120B and 120C and the sensing device 60 protrude into the internal cavity 136, with the sensing devices 60 protruding farther, though any of the configurations discussed in reference to FIGS. 5 and 6 could also be present in the embodiments of FIGS. 7 through 9.

FIGS. 10 through 14 show another bolt-type anchor 120D adapted to be placed in a wall of an organ, similar to that shown for the bolt-type anchors 120B and 120C of FIGS. 7-9. The embodiment of the anchor 120D shown in FIGS. 10 through 14 has a tubular portion 162 and a disk-shaped portion 164 at oppositely-disposed distal and proximal ends, respectively, of the anchor 120D, and an internal passage 166 sized to accommodate at least a portion of a sensing device, such as the sensing device 60 of FIG. 4. The passage 166 preferably has a shape that is complementary or otherwise corresponds to the outer shape of a sensing device intended to be placed therein, for example, a cylindrical shape corresponding to the cylindrical outer shape of the sensing device 60, though passages and sensing devices of other and even different shapes are also within the scope of the invention. In the particular embodiment shown in FIGS. 10-14, a proximal portion of the passage 166 defines a proximal opening 168 at a proximal surface 178 of the disk-shaped portion 164, and a distal portion of the passage 166 within the tubular portion 162 defines a distal opening 170 at the distal end of the anchor 120D. Also in the illustrated embodiment, the distal opening 170 is configured for retaining the sensing device 60 within the passage 166, and the proximal opening 168 is sized to enable the sensing device 60 to pass therethrough into the passage 166 until the device 60 abuts a feature 172 at the distal opening 170. As a nonlimiting example, the proximal and distal openings 168 and 170 represented in FIGS. 10 through 14 are both circular in shape, and the distal opening 170 is smaller than the proximal opening 168 as a result of the feature 172 being in the form of a radially inward-extending peripheral lip or rim that surrounds the distal opening 170. It is also within the scope of the invention that the feature 172 (or multiple features) could take other forms, for example, as a result of the distal opening 170 being sized to create an interference fit with the device 60, one or more flanges or tabs that extend radially inward over the distal opening 170 of the passage 166, an adhesive bond formed with a biocompatible epoxy, glue, or cement, etc.

Figure 10:
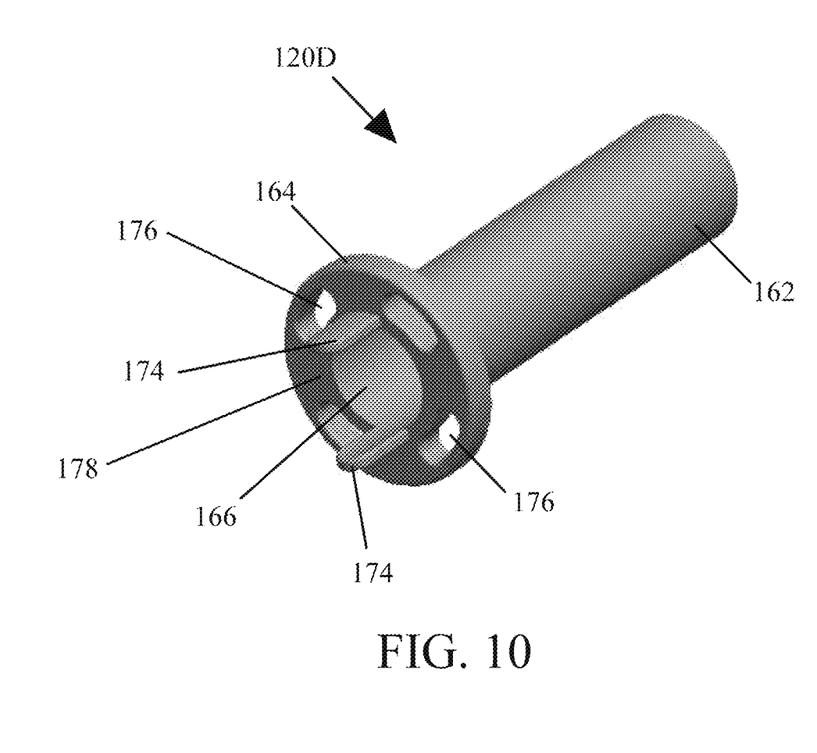
FIG. 10 schematically represents a perspective view of an alternative bolt-type anchor capable of use with the sensing device of FIG. 4 to form a sensing unit in accordance with additional embodiments of the invention.
Figure 11:
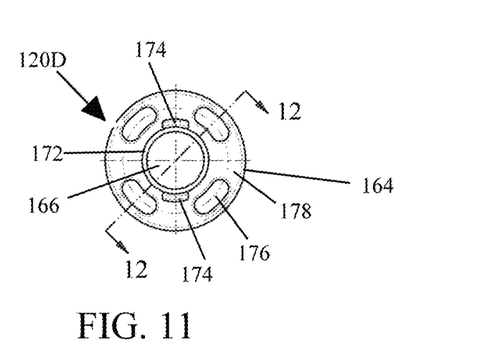
FIG. 11 is a proximal end view of the bolt-type anchor of FIG. 10.
Figure 12:
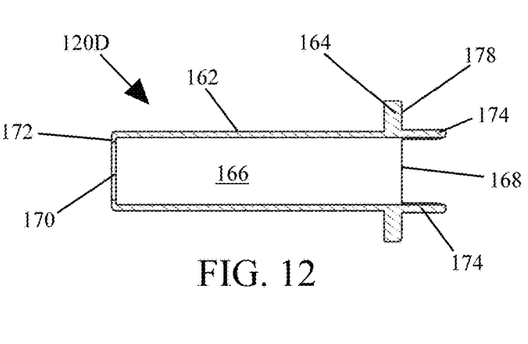
Figure 13:
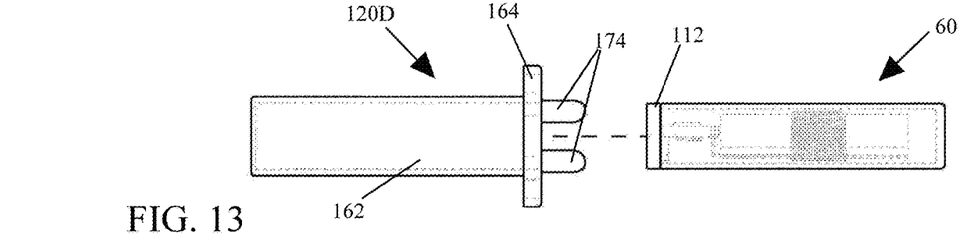
Figure 14:
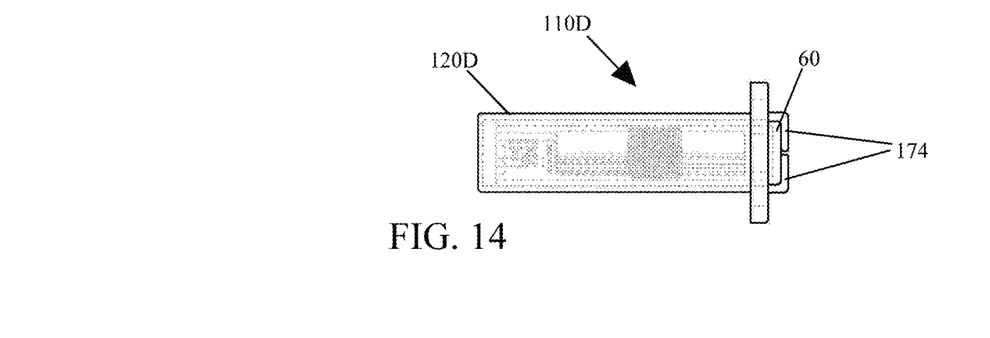

As represented in FIG. 13, inserting the sensing device 60 into the tubular portion 162 through the disk-shaped portion 164, and therefore through the proximal end of the anchor 120D, yields a sensing unit 110D represented in FIG. 14. The sensing device 60 is shown as being further secured within the tubular portion 162 by one or more features 174 disposed on the disk-shaped portion 164. Depending on the particular feature 172 provided at the distal opening 170 of the anchor 162, such a feature 174 could be the result of the disk-shaped portion 164 closing the proximal portion of the passage 166, in which case the sensing device 60 would be inserted into the tubular portion 162 through the distal opening 170 of the anchor 120D similar to that shown for the anchors 120B and 120C in FIGS. 8 and 9. On the other hand, the nonlimiting embodiment of FIGS. 10-14 represents the feature 174 as a diametrically-opposed pair of flanges, tabs, or "ears" disposed on the disk-shaped portion 164, which are shown in FIGS. 10, 12 and 13 as originally extending from the proximal surface 178 of the disk-shaped portion 164 in an axial direction of the tubular portion 162. By plastically bending or otherwise deforming the features 174 toward each other after the sensing device 60 is placed in the passage 166 through the proximal opening 168, the features 174 are able to secure the sensing device 60 within the passage 166 of the tubular portion 162 by extending radially inward over the proximal opening 168 of the passage 166, thereby capturing the device 60 between the features 172 and 174 at the distal and proximal ends of the anchor 120D. The entire anchor 120D or at least the features 174 thereof can be fabricated from various materials that are capable of contributing the desired plastic deformability of the features 174, a nonlimiting example of which is PEEK.

The sensing unit 110D can be placed in a wall of an internal organ (e.g., hear, artery, aneurysm sac, etc.) similar to what was described above for the embodiments of FIGS. 5 through 9. As such, the tubular portion 162 of the anchor 120D is placed within and passes at least partially through the wall 134 (for example, the endocardium lining a chamber of the heart), while the disk-shaped portion 164, which surrounds and projects radially from the tubular portion 162, remains outside the organ and abuts the external surface 142 of the wall 134. In the nonlimiting example of FIGS. 10-14, the tubular portion 162 has an outer cylindrical shape that may facilitate implantation of the anchor 120D and occlusion of an opening in which the unit 110D is placed. For this reason, the tubular portion 162 also preferably defines a continuous annular-shaped wall that entirely surrounds the distal portion of the passage 166 therein, so that the passage 166 is entirely closed except for its proximal and distal openings 168 and 170. The length of the tubular portion 162 can be selected based on the thickness of the wall in which the unit 110D is to be placed, and based on whether the distal end of the unit 110D defined by the tubular portion 162 is intended to protrude beyond the internal surface 138 of the wall 134 into the cavity 136. The distal end of the unit 110D (i.e., the lefthand end of the anchor 120D in FIG. 14) may protrude from the internal surface 138, for example, not more than one centimeter, and preferably not more than eight millimeters. Alternatively, the unit 110D may be placed in the wall 134 so as not to protrude beyond the internal surface 138, for example, the distal end of the unit 110D may be recessed within the wall 134, for example, up to about two millimeters from the internal surface 138. As a result of assembling the anchor 120D and sensing device 60 in the manner shown in FIGS. 13 and 14, the distal face 112 of the device 60 that carries the transducer 62 does not protrude from the passage 166 of the anchor 120D, yet is exposed within the distal opening 170 of the anchor 120D, such that the distal end of the anchor 120D protrudes farther into the cavity 136 than the sensing device 60 by a distance defined by the axial dimension of the feature 172.

In view of the above discussion, and similar to the anchor 120B, only the tubular portion 162 of the anchor 120D is inserted into an incision made in a wall of an internal organ, the disk-shaped portion 164 remains entirely outside the incision, and the tubular and disk-shaped portions 162 and 164 do not to clamp the wall 134 therebetween. The disk-shaped portion 164 can be configured to enable the anchor 120D to be secured to an organ wall using various techniques, such as with standard surgical sutures, nails, screws, springs, and biocompatible adhesives such as cements, glues, epoxies, etc. In the embodiment of FIGS. 10-14, multiple openings 176 are defined in the disk-shaped portion 164 to enable the anchor 120D to be secured to an organ wall with sutures. The openings 176 are shown as having an oblong shape so as to be longer in the circumferential direction of the disk-shaped portion 164 than in the radial direction. If used to secure sutures, an even number of openings 176 are preferably provided to reduce the risk of surgical error. A recess can be formed in the disk-shaped portion 164 to hold sutures nuts (not shown) in place and thereby reduce irritation to the organ wall 134, for example, the pericardium if placed in the heart. Particularly suitable implantation processes are believed to include the placement of the sensor unit 110D in an opening created by a scalpel or needle (or another instrument capable of puncturing the organ wall). In each case, sutures are preferably placed in the wall 134 surrounding the location where the opening is to be created. For example, a combination of pursestring and rail sutures may be used. If the opening is to be created with a scalpel, the scalpel is used to create an incision through the wall at or near the center of the sutures, and the sensor unit 110D is placed in the incision. If the opening is created with a needle, the needle is used to puncture the wall at or near the center of the sutures, and the opening is dilated prior to placement of the sensor unit 110D in the opening. In each case, the sutures can be tightened after sensor placement to assist in securing the unit 110D to the wall 134. Though employing a slightly more involved technique, placing the unit 110D in a dilated opening initially formed with a needle can minimize damage to tissue and reduce bleeding during placement of the unit 110D.

In accordance with a preferred aspect of the invention, the sensing device 60 can be implanted to monitor a variety of physiological parameters. For example, the device 60 can be used to monitor radial artery pressure. In this embodiment, the sensing device 60 can be implanted with one of the anchors 120A-D under the skin of the wrist above the radial artery, while the readout unit 80 is located outside the body. The device 60 may contain the antenna 66 (FIG. 2a) or the antenna 66 may be located elsewhere in the arm or body (FIG. 2b). The readout unit 80 or portions thereof can be located on the outside of the body in close proximity to the device 60, for example, worn on the wrist of the patient similar to a wrist watch.

The sensing device 60 can also be used to monitor intrasac pressures in an aneurysm sac of a patient who has had surgery to repair an abdominal aortic aneurysm or a thoracic aortic aneurysm. In this embodiment, the sensing device 60 can be implanted with one of the anchors 120A-D placed in the wall of the aneurysm sac, while the readout unit 80 is located outside the body. The device 60 may contain the antenna 66 (FIG. 2a) or the antenna 66 may be located elsewhere in the arm or body (FIG. 2b). The readout unit 80 or portions thereof can be located on the outside of the body in close proximity to the device 60, for example, worn on a belt.

Another example is to use the sensing device 60 to monitor intracranial pressures in patients with traumatic brain injuries (blunt trauma or penetrating trauma), including but not limited to patients with intracranial hemorrhage, closed head injuries, epidural hematoma, subdural hematoma, subarachnoid hemorrhage, diffuse axonal injury, and intracranial hypertension. Depending on the type of injury, the sensing device 60 can be implanted with one of its anchors 120A-D, preferably the anchor 120D, using a minimally-invasive surgery technique into any area of the brain to place the distal face 112 of the device 60 (carrying the transducer 62) in contact with either brain tissue or fluid. Portions of the readout unit 80 and optionally the antenna 66 of the sensing device 60 can be implanted between the skull and scalp of the patient.

Still another example is to use the sensing device 60 to monitor pulmonary artery pressures and other cardiovascular pressures near or within the heart. For example, the sensing device 60 can be implanted with one of its anchors 120A-D, preferably the anchor 120D, through the outer wall of the right ventricle, left ventricle, right atrium, left atrium, left ventricular apex, right ventricular apex, left atrial appendage, right atrial appendage, pulmonary artery, etc. As particular examples, the sensing device 60 can be implanted in the ventricular apex (right or left) or the atrial appendage (left or right), with the distal face 112 of the device 60 (carrying the transducer 62) exposed within the ventricle or atrium. In each case, the risk of complications inside the heart, in particular thrombosis and thrombogenicity, are greatly reduced.

In each of the above-noted embodiments and applications, the anchors 120A-D can be modified to provide other features beyond those described, for example, a device similar to an RFID tag can be added to any one of the anchors 120A-D such that it wirelessly transmits ID information concerning the sensing device 60. The ID information may include an ID number, ID name, patient name/ID, calibration coefficients/information, range of operation, date of implantation, valid life of the device (operation life), etc. The anchors 120A-D may further include additional capabilities such as features for connection to a catheter, shunt, or other device (not shown).

In addition to the sensing units 110A-D and reader unit 80 described above, the monitoring systems of this invention can be combined with other technologies to achieve additional functionalities. For example, the reader unit 80 can be implemented to have a remote transmission capability, such as home monitoring that may employ telephone, wireless communication, or web-based delivery of information received from the sensing units 110A-D by the reader unit 80 to a physician or caregiver. In this manner, the reader unit 80 can be adapted for remote monitoring of the organ and patient, closed-loop drug delivery of medications to treat the organ, closed-loop pacemaker parameter tuning to treat congestive heart failure or congestive heart failure related conditions, warning of critical worsening of congestive heart failure or congestive heart failure related conditions, portable or ambulatory monitoring or diagnosis, monitoring of battery operation, data storage, reporting global positioning coordinates for emergency applications, and communication with other medical devices chosen from the group consisting of pacemakers, left ventricular assist devices (LVAD), defibrillators, cardioverter defibrillators, drug delivery systems, non-drug delivery systems, and wireless medical management systems. Furthermore, the placement of the sensing units 110A-D can be utilized as part of a variety of different medical procedures, including early diagnosis of a heart failing due to congestive heart failure related conditions, early diagnosis of failure of the organ, early intervention in treatment of congestive heart failure related conditions, tailoring of medications, disease management, identification of complications from congestive heart failure related conditions, identification of complications from cardiovascular disease related conditions, treatment of complications from congestive heart failure related conditions, treatment of complications from cardiovascular disease related conditions, pacing adjustments to the heart, reduction in frequency and severity of hospitalizations due to cardiovascular diseases, reduction in frequency and severity of hospitalizations due to congestive heart failure, tuning of defibrillator or pacemaker parameters to improve congestive heart failure related conditions, identification of mitral valve stenosis, treatment of mitral valve stenosis, feedback regarding the impact of medication on the organ, and chronic disease management of the organ.

While the invention has been described in terms of specific embodiments, it is apparent that other forms could be adopted by one skilled in the art. As nonlimiting examples, the configurations of the sensing device 60 and anchors 120A-D could differ from what those depicted in the drawings. Therefore, the scope of the invention is to be limited only by the following claims.

The invention claimed is:

1. An anchor for placing a sensing device through a wall of an internal organ of a living body to sense a physiological parameter in an internal cavity of the organ, the anchor comprising:
   a tubular portion defining a distal end of the anchor;
   a disk-shaped portion having a proximal surface at a proximal end of the anchor, the disk-shaped portion surrounding and projecting radially from the tubular portion;
   an internal passage within the tubular and disk-shaped portions for receiving the sensing device, the internal passage having a distal portion that defines a distal opening in the tubular portion at the distal end of the anchor and having a proximal portion that defines a proximal opening in the proximal surface of the disk-shaped portion at the proximal end of the anchor, the distal opening being smaller than the proximal opening so that the sensing device inserted through the proximal opening into the internal passage passes through the internal passage until the sensing device abuts the distal end of the anchor at the distal opening;
   means at the proximal end of the anchor for retaining the sensing device within the internal passage, the retaining means comprising at least one feature disposed on the disk-shaped portion, extending from the proximal surface of the disk-shaped portion in an axial direction of the tubular portion, and plastically deformable to capture the sensing device between the at least one feature and the distal end of the tubular portion; and
   means on the disk-shaped portion for securing the anchor to the wall of the internal organ.

2. The anchor according to claim 1, wherein the internal passage has a shape complementary to an external shape of the sensing device.

3. The anhcor according to claim 2, wherein the shape of the internal passage and the external shape of the sensing device are cylindrical.

4. The anchor according to claim 1, wherein the tubular portion defines a continuous annular-shaped wall that entirely surrounds the distal portion of the internal passage therein.

5. The anchor according to claim 1, wherein the internal passage is entirely closed except for the proximal and distal openings.

6. The anchor according to claim 5, wherein the distal end of the tubular portion defines a radially inward-extending peripheral rim that surrounds the distal opening to cause the distal opening to be smaller than the proximal opening.

7. The anchor according to claim 1, wherein the at least one feature comprises at least one pair of diametrically-opposed tabs disposed on the disk-shaped portion and extending from the proximal surface of the disk-shaped portion in the axial direction of the tubular portion.

8. The anchor according to claim 7, wherein the tabs are plastically deformable toward each other and over the proximal opening to secure the sensing device within the internal passage.

9. The anchor according to claim 1, wherein the means for securing the anchor to the wall of the internal organ comprises suture openings in the disk-shaped portion.

10. The anchor according to claim 1, wherein the anchor is entirely formed of a biocompatible material.

11. The anchor according to claim 1, wherein the sensing device is within the internal passage and secured therein to define a sensing unit, the sensing device has a sensing element exposed within the distal opening of the anchor, and the sensing device does not protrude through the distal opening such that the tubular portion defines a distal end of the sensing unit.

12. A minimally-invasive surgical procedure that uses the anchor of claim 1 to place the sensing device through the wall of the internal organ to sense a physiological parameter within the internal cavity of the organ, the procedure comprising:
   providing a sensing unit by placing the sensing device within the internal passage of the anchor by inserting the sensing device through the proximal opening in the proximal surface of the disk-shaped portion, passing the sensing device through the internal passage until the sensing device abuts the distal end of the anchor at the distal opening, and then securing the sensing device within the internal passage with the means at the proximal end for retaining the sensing device, the sensing device comprising a sensing element adapted to sense the physiological parameter within the organ, the sensing element being exposed within the distal opening of the anchor;
   making an incision in the living body to enable access to the organ;
   inserting an instrument through the incision and making an opening therewith through the wall of the organ and into the internal cavity thereof;
   placing the sensing unit in the opening in the wall of the organ such that the distal opening of the anchor is exposed to the internal cavity of the organ, at least part of the tubular portion of the anchor is within the wall of the organ, and the disk-shaped portion of the anchor is outside the organ and abuts an external surface of the wall of the organ; and
   securing the anchor to the wall of the organ such that the sensing device is secured within the opening in the wall of the organ by only the anchor and the opening is occluded by the tubular portion of the anchor.

13. The minimally-invasive surgical procedure according to claim 12, further comprising telemetrically communicating with the sensing device to obtain a reading of the physiological parameter using a readout device located outside the living body.

14. The minimally-invasive surgical procedure according to claim 12, wherein the organ is chosen from the group consisting of a heart, blood vessel, meninges, kidney, lung, bladder, and abdominal wall.

15. The minimally-invasive surgical procedure according to claim 12, wherein the sensing element of the sensing device is recessed beneath an interior lining of the internal cavity, or is substantially flush with the interior lining, or extends into the internal cavity not more than one centimeter beyond the interior lining.

16. The minimally-invasive surgical procedure according to claim 12, wherein the sensing device passes through the internal passage until the sensing device abuts a radially inward-extending peripheral rim that surrounds the distal opening at the distal end of the anchor.

17. The minimally-invasive surgical procedure according to claim 12, wherein the organ is a heart and the internal cavity is a chamber of the heart.

18. The minimally-invasive surgical procedure according to claim 12, wherein the securing step comprises suturing the disk-shaped portion of the anchor to the wall of the organ.

19. The minimally-invasive surgical procedure according to claim 12, wherein the instrument is a needle and the step of making the opening therewith comprises puncturing the wall of the organ with the needle and then dilating the opening to receive the tubular portion of the anchor.

20. The minimally-invasive surgical procedure according to claim 12, wherein the instrument is a scalpel and the step of making the opening therewith comprises making an incision in the wall of the organ with the scalpel.

21. The minimally-invasive surgical procedure according to claim 12, wherein the tubular and disk-shaped portions do not clamp the wall therebetween.

22. The minimally-invasive surgical procedure according to claim 12, wherein the physiological parameter is at least one chosen from the group consisting of pressure, temperature, flow, acceleration, vibration, composition of a biological fluid, oxygen content of a biological fluid, carbon dioxide content of a biological fluid, glucose content of a biological fluid, gene content of a biological fluid, hormone content of a biological fluid, and gas content of a biological fluid.

23. The minimally-invasive surgical procedure according to claim 12, wherein the minimally-invasive surgical procedure is part of at least one of the following medical procedures: diagnosis of chronic diseases; diagnosis of a heart failing due to congestive heart failure related conditions; diagnosis of failure of the organ; intervention in treatment of congestive heart failure related conditions; tailoring of medications; disease management; identification of complications from congestive heart failure related conditions; identification of complications from cardiovascular disease related conditions; treatment of complications from congestive heart failure related conditions; treatment of complications from cardiovascular disease related conditions; pacing adjustments to the heart; reduction in frequency and severity of hospitalizations due to cardiovascular diseases; reduction in frequency and severity of hospitalizations due to congestive heart failure; tuning of defibrillator or pacemaker parameters to improve congestive heart failure related conditions; identification of mitral valve stenosis; treatment of mitral valve stenosis, feedback regarding the impact of medication on the organ; and chronic disease management of the organ.

24. The minimally-invasive surgical procedure according to claim 12, wherein the sensing device further comprises a telemetry antenna for telemetrically communicating with a readout device.

25. The minimally-invasive surgical procedure according to claim 24, wherein the readout device is used to perform at least one of the following: remote monitoring of the organ and the living body, remote monitoring of the organ and the living body with a telephone-based data and information delivery system; remote monitoring of the organ and the living body with a wireless telephone-based data and information delivery system; remote monitoring of the organ and the living body with an Internet-based data and information delivery system; closed-loop drug delivery of medications to treat the organ; closed-loop pacemaker parameter tuning to treat congestive heart failure or congestive heart failure related conditions; warning of critical worsening of congestive heart failure or congestive heart failure related conditions; portable or ambulatory monitoring or diagnosis; monitoring of battery operation; data storage; reporting global positioning coordinates for emergency applications; and communication with other medical devices chosen from the group consisting of pacemakers, left ventricular assist devices, defibrillators, cardioverter defibrillators, drug delivery systems, non-drug delivery systems, and wireless medical management systems.

* * * * *